United States Patent
Nebolsin

(10) Patent No.: US 11,414,377 B2
(45) Date of Patent: Aug. 16, 2022

(54) MODULATOR OF METABOTROPIC AND IONOTROPIC TRANSMEMBRANE RECEPTORS AND USE THEREOF

(71) Applicant: IBD THERAPEUTICS LLC, Moscow (RU)

(72) Inventor: Vladimir Evgenievich Nebolsin, Oblast (RU)

(73) Assignee: IBD THERAPEUTICS LLC, Moscow (RU)

( * ) Notice: Subject to any disclaimer, the term of this patent is extended or adjusted under 35 U.S.C. 154(b) by 13 days.

(21) Appl. No.: 17/054,686

(22) PCT Filed: May 7, 2019

(86) PCT No.: PCT/RU2019/050060
§ 371 (c)(1),
(2) Date: Nov. 11, 2020

(87) PCT Pub. No.: WO2019/216795
PCT Pub. Date: Nov. 14, 2019

(65) Prior Publication Data
US 2021/0070692 A1 Mar. 11, 2021

(30) Foreign Application Priority Data
May 11, 2018 (RU) .......................... RU2018117463

(51) Int. Cl.
| | |
|---|---|
| *C07C 237/22* | (2006.01) |
| *A61P 1/12* | (2006.01) |
| *A61P 25/00* | (2006.01) |
| *A61P 11/14* | (2006.01) |
| *C07C 231/02* | (2006.01) |
| *A61K 45/06* | (2006.01) |

(52) U.S. Cl.
CPC .............. *C07C 237/22* (2013.01); *A61P 1/12* (2018.01); *A61P 11/14* (2018.01); *A61P 25/00* (2018.01); *C07C 231/02* (2013.01); *A61K 45/06* (2013.01)

(58) Field of Classification Search
CPC .................................................. C07C 237/22
See application file for complete search history.

(56) References Cited

U.S. PATENT DOCUMENTS 4,579,841 A * 4/1986 Stewart .............. C07K 5/06078
260/1

FOREIGN PATENT DOCUMENTS

WO WO-2019216795 A1 * 11/2019 ........... A61K 31/165

* cited by examiner

*Primary Examiner* — Yong S. Chong
(74) *Attorney, Agent, or Firm* — BCF LLP

(57) ABSTRACT

The invention relates to organic chemistry, pharmacology and medicine and is concerned with the treatment of inflammatory and autoimmune diseases, such as psoriasis, atopic dermatitis, prurigo, Crohn's disease, colitis, gastrointestinal diseases such as diarrhoea and irritable bowel syndrome, respiratory diseases such as asthma, COPD, bronchitis, rhinitis, and also cough and a series of other diseases associated with the activity of opioid and tachykinin receptors and of TRPV1 and TRPM8 ion channels using a 2-phenylethylamine N-(p-hydroxyphenylacetyl)phenylalanine compound

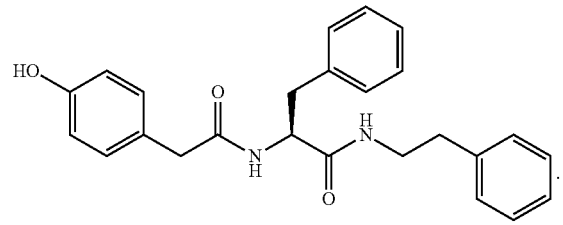

The invention, and also pharmaceutically acceptable adducts, hydrates, solvates are agonists of opioid receptors, antagonists of tachykinin receptors and of TRPV1 and TRPM8 ion channels. The invention also relates to pharmaceutical compositions comprising a therapeutically effective amount of the compound according to the invention.

8 Claims, No Drawings

MODULATOR OF METABOTROPIC AND IONOTROPIC TRANSMEMBRANE RECEPTORS AND USE THEREOF

CROSS REFERENCE TO RELATED APPLICATIONS

This application is a U.S. national stage application under 35 U.S.C. § 371 of International Application No. PCT/RU2019/050060, filed May 7, 2019, which claims the priority of the RU Application No. 2018117463, filed May 11, 2018.

FIELD OF THE INVENTION

The present invention relates to organic chemistry, pharmacology and medicine and is concerned with the treatment of inflammatory and autoimmune diseases, gastrointestinal diseases, respiratory tract diseases, cough and a series of other diseases by using a compound that is a modulator of metabotropic and ionotropic transmembrane receptors involved, in particular, in nociception, vasodilatation, neurogenic inflammation development and chemotaxis of immune system cells.

BACKGROUND OF THE INVENTION

Metabotropic and ionotropic transmembrane receptors are the two largest groups of proteins regulating nociception, vasodilatation, inflammation and other important processes in the body of animals and human. Biological effects of the majority of transmembrane receptors are realized due to interacting with endogenous modulators activating or suppressing the activity of the corresponding cell receptors.

In particular, endogenous tachykinins and opioids are groups of neuropeptides involved in the development of neurogenic inflammation and pruritus, nociception, vasodilatation, contraction of muscle fibres and chemotaxis of immune system cells. Biological effects of endogenous tachykinins and opioids are realized due to the interaction with tachykinin (neurokinin) and opioid metabotropic receptors. These receptors conjugated to G-protein are widespread in the central and peripheral nervous systems and are predominantly localized in primary afferent neurons located in the respiratory and urinary tracts (Life Sci. 2000; 66(23): 2221-31), as well as in the gastrointestinal tract (Curr Opin Endocrinol Diabetes Obes. 2016 February; 23(1):3-10; Cell Tissue Res. 2014 May; 356(2):319-32), papillary dermis and other skin compartments (J Comp Neurol. 1999 Jun. 14; 408(4):567-79; Physiol Rev. 2014 January; 94(1):265-301). The modulation of the activity of tachykinin and opioid receptors of the peripheral nervous system is associated with the wide spectrum of biological effects.

In the gastrointestinal tract (GIT), opioid and tachykinin receptors are predominantly expressed on lamina muscularis mucosa cells, immune cells, and in neurons of submucosa and muscle plexus (J Comp Neurol, 2007, 503, 381-91; Regul Pept. 2009 Jun. 5; 155(1-3): 11-7). The modulation of the activity of opioid and tachykinin receptors in the GIT has an influence on the intestinal motility, the secretory and immune activities, visceral sensitivity and nociception (Holzer P. Tachykinins. In Handbook of Biologically Active Peptides (Second Edition); Kastin A. J., Ed.; Elsevier, 2013; pp. 1330-1337; Regul Pept. 2009 Jun. 5; 155(1-3):11-7). Thus, for example, the activation of µ-opioid receptors (MOR) in the GIT results in the reduction of abdominal pain and visceral hyperalgesia (Biochemical Pharmacology 92 (2014) 448-456). At the same time, the suppression of peripheral $NK_3$ receptor activity as shown in animals (Neurogastroenterol Motil, 2003, 15, 363-9; Neurogastroenterol Motil, 2004, 16, 223-31), reduces nociception caused by colorectal tension, and also stress-induced hypersensitivity. $NK_1$ and $NK_2$ tachykinin receptors, as well as µ-opioid receptors have the pronounced effect on GIT motility (Pharmacol Ther, 1997, 73, 173-217; Expert Opin Investig Drugs. 2007 February; 16(2):181-94), in view of which these receptors are the most perspective targets for the treatment of functional bowel diseases and in particular diarrhoea. In a number of preclinical and clinical studies, it has been shown that the activation of opioid receptors and the suppression of tachykinin receptor activity reduces the secretion of ions and fluid, delays the transit through the small intestine and large intestine, and increases pressure in the anal sphincter (Expert Opin Investig Drugs. 2007 February; 16(2):181-94; Pharmacol Ther, 1997, 73, 173-217).

It is important to note that the double and triple tachykinin receptor antagonists apparently are more effective than selective antagonists in the treatment of gastrointestinal disorders. Thus, for example, it has been shown that selective tachykinin receptor antagonists have the significant effect on the gut motility of animals only when the cholinergic component is blocked (Holzer P. Role of tachykinins in the gastrointestinal tract. In: Holzer P, editor. Tachykinins. Handbook of experimental pharmacology, vol. 164. Berlin: Springer; 2004. p. 511-58). However, while simultaneously blocking all three tachykinin receptors, the peristaltic in the lower large intestine of the guinea pig was also significantly reduced without the participation of antagonists of acetylcholinesterase receptors (Gastroenterology, 2001, 120, 938-45).

Thus, modulators of opioid and tachykinin receptors can be used for the therapy of a number of functional and inflammatory diseases of the GIT such as diarrhoea, irritable bowel syndrome, colitis, Crohn's disease, etc. Moreover, the simultaneous action on opioid and tachykinin receptors can provide the synergistic effect in the treatment of chronic abdominal pain and functional disorders of the GIT (J Med Chem. 2011 Apr. 14; 54(7): 2029-2038). Furthermore, the simultaneous action on the signaling of opioid and tachykinin receptors potentially allows of using low doses of the preparation and reducing the incidence of side effects typical for the opioid therapy (Regul Pept. 2009 Jun. 5; 155(1-3): 11-7).

Modulators of opioid and tachykinin receptors can also be used for the therapy of respiratory tract diseases. In particular, tachykinins are potent constrictors of airway smooth muscles. Furthermore, the action of tachykinins on vascular endothelial cells cause the progression of vasodilatation and increase vascular permeability of the microcirculatory bloodstream of respiratory tracts (Drug News Perspect 1998, 11(8): 480; BMC Pulm Med. 2011 Aug. 2; 11:41). In addition, tachykinins increase the secretion of mucous glands and epithelial cells of the respiratory tracts (Pflugers Arch. 2008 November; 457(2):529-37; Physiol Rev. 2015 October; 95(4):1241-319) and are potent chemoattractants and activators of immune system cells in the respiratory tract tissues (Drug News Perspect. 1998 October; 11(8):480-9; Trends Immunol. 2009 June; 30(6):271-6). Tachykinins and opioids modulate the various lung reflexes, including cough reflex (Pharmacol Ther. 2009 December; 124(3):354-75; Am J Physiol Regul Integr Comp Physiol. 2000 October; 279(4):R1215-23; Am J Respir Crit Care Med. 1998 July; 158(1):42-8), parasympathetic, cholinergic, bronchoconstrictor reflexes (Nat Neurosci. 2012 Jul. 26; 15(8):1063-7;

Prog Histochem Cytochem. 2010 February; 44(4):173-202). The pathophysiological role of tachykinins in respiratory tract diseases apparently is mediated by the activation of $NK_1$ and $NK_2$ receptors, whereas the activation of $NK_2$ and $NK_3$ receptors participates in the pathogenesis of cough (Am J Respir Crit Care Med. 1998 July; 158(1):42-8; Eur J Pharmacol. 2002 Aug. 23; 450(2):191-202). Furthermore, tachykinins appear to effectively modulate the activity of the ionotropic receptors (Neuropeptides. 2010 February; 44(1): 57-61), in particular, TRPV1 and TRPM8 ion channels involved in the detection and regulation of temperature sensory perception and expressed in primary afferent neurons and in surrounding tissues of the respiratory tract (Gut. 2008 July; 57(7):923-9; *J Neurosci.* 2008 Jan. 16; 28(3): 566-75). In addition to the involvement of TRPV1 in the pathogenesis of cough and rhinitis, it plays the important role in the development of pain sensitivity (Expert Opin Ther Pat. 2012 June; 22(6):663-95; Recent Pat CNS Drug Discov. 2013 December; 8(3):180-204; Expert Opin Investig Drugs. 2012 September; 21(9):1351-69). In a number of clinical studies and in animal models, it has been shown that the administration of TRPV1 ion channel antagonists increases the threshold response to cough (J Allergy Clin Immunol. 2014 July; 134(1):56-62), and also reduces the intensity of symptoms of COPD (Am J Respir Crit Care Med. 2016 Jun. 15; 193(12):1364-72; Sci Transl Med. 2012 Nov. 7; 4(159):159ra147) and asthma (Br J Pharmacol. 2012 July; 166(6):1822-32). At the same time, it is important to note that tachykinin and opioid receptors are connected to the TRPV1 ion channels by a complex feedback system. Thus, for example, the activation of the TRPV1 results in the development of tolerance to opioid analgesics (Channels (Austin). 2015; 9(5):235-43). For this reason, the activation of opioid receptors with the simultaneous suppression of TRPV1 ion channel activity is an effective strategy for treating pain symptoms of various diseases. On the other hand, the suppression of the activity of the TRPV1 ion channel results in the reduction in the production of tachykinins and the decrease in the intensity of neurogenic inflammation (Pulm Pharmacol Ther. 2018 April; 49:1-9). In contrast to the TRPV1 ion channel activated by a high temperature, a TRPM8 ion channel is activated at a temperature of surrounding tissues of below 30° C. The activation of the TRPM8 results in the enhanced expression of proinflammatory cytokines and the hypersecretion of mucus by human bronchial epithelial cells (Inflammation. 2018 August; 41(4):1266-1275) and nasal cavity (Medicine (Baltimore). 2017 August; 96(31):e7640). Thus, the activation of opioid receptors, together with the suppression of the activity of tachykinin receptors and TRPV1 and TRPM8 ion channels, may have the synergistic effect in the treatment of cough as the characteristic symptom for a number of respiratory tract diseases such as asthma, pulmonary fibrosis, COPD and bronchitis. It is important to note that, according to literary data, modulators of opioid and tachykinin receptors, TRPV1 and TRPM8 ion channels may have the direct pathogenetic action on these respiratory tract diseases. Thus, in particular, it has been shown in clinical studies that tachykinin receptor antagonists inhibit bronchospasm and reduce airway hyperreactivity in patients with asthma (Eur Respir J. 2004 January; 23(1):76-81; Pulm Pharmacol Ther. 2006; 19(6):413-8; BMC Pulm Med. 2011 Aug. 2; 11:41). In patients with COPD morphine inhalations resulted in the substantial relief of shortbreathing and other symptoms of the disease (BMC Pulm Med. 2017 Dec. 11; 17(1):186).

Modulators of opioid and tachykinin receptors and TRPV1 and TRPM8 ion channels can also be used in the therapy of inflammatory and autoimmune diseases, in particular for the therapy of pruritus in psoriasis and atypical dermatitis (Br J Dermatol. 2019 Jan. 8, J Am Acad Dermatol. 2018 March; 78) and pain symptomatic in Crohn's disease and ulcerative colitis (Pharmaceuticals (Basel). 2019 Mar. 30; 12(2); Inflamm Bowel Dis. 2015 February; 21(2):419-27). The activation of TRPV1 ion channels located at sensory nerve endings and surrounding tissues of the skin results in the significant increase in the production of substance P and other endogenous tachykinins and in the development of neurogenic inflammation (Br J Dermatol. 2019 Jan. 8). Moreover, the increased production of substance P results in the $NK_1$-mediated activation of mast cells, the increase in the production of tumor necrosis factor and the development of pruritus (J Am Acad Dermatol. 2018 March; 78(3 Suppl 1):S63-S66). In clinical studies, the involvement of substance P and $NK_1$ receptors in the development of prurigo was shown, wherein the $NK_1$ receptor antagonist reliably reduced the intensity of disease symptoms compared to baseline values (Acta Derm Venereol. 2018 Jan. 12; 98(1):26-31). Thus, the suppression of the activity of TRPV1 ion channels and tachykinin receptors is the possible therapeutic approach to treat atopic dermatitis, prurigo and other diseases accompanied with the development of pruritus.

It is possible to conclude on the basis of literary data that the strategy directed to the activation of opioid receptors with the simultaneous suppression of activity of tachykinin receptors, TRPV1 and TRPM8 ion channels is the possible approach to the treatment of inflammatory and autoimmune diseases (such as psoriasis, atopic dermatitis, Crohn's disease and ulcerative colitis), gastrointestinal diseases (such as irritable bowel syndrome, colitis and postoperative intestinal obstruction), respiratory tract diseases (such as asthma, COPD, bronchitis, rhinitis) and cough, including cough in case of pulmonary fibrosis, bronchitis, asthma, COPD and other diseases.

Various agonists of opioid receptor, antagonists of tachykinin receptor, and antagonists of TRPV1 and TRPM8 ion channels, including selective $NK_1$ antagonists and mixed $NK_1/NK_2$ antagonists of receptors based on high affine 3-cyano-1-naphthamide derivatives (WO2001077089, WO2002026724) or naphthoic acid amide (WO2001077069, WO2000059873) are known to date. It is important to note that no compounds which are agonists of opioid receptors, antagonists of tachykinin receptors and of TRPV1 and TRPM8 ion channels are described in the scientific literature. As examples of the close inventions, it is possible to indicate workings of Boehringer Ingelheim company, which mainly relate to arylglycinamide derivatives (EP1295599) for the treatment of inflammatory skin diseases. Menarini Group company performs the development of a glycosylated bicyclic cyclohexapeptide antagonist of $NK_2$-receptor for the treatment of irritable bowel syndrome (Br J Pharmacol. 2001 September; 134(1):215-23, Eur J Pharmacol. 2006 Nov. 7; 549(1-3):140-8). The closest analogues of the compound that is the object of the present invention are given in publications from Ciba-Geigy company (WO1996026183). Non-selective antagonists of tachykinin receptors comprising phenylalanine derivatives for the treatment of central nervous system diseases are described herein. However, in the structures of the compounds published by the Ciba-Geigy company ligands contain two ester substituents which significantly reduce the metabolic stability of the compound.

Thus, to date there is no drug acting as an agonist of opioid receptors, antagonist of tachykinin receptors and of TRPV1 and TRPM8 ion channels, which would be used in the therapy of inflammatory and autoimmune diseases, gastrointestinal, pulmonary and respiratory diseases. Therefore, still there is a need for the development and introduction into clinical practice of new effective drugs comprising modulators of opioid and tachykinin receptors, as well as TRPV1 and TRPM8 ion channels.

The present invention relates to the obtainment and use of a novel chemical compound which is effective in the activation of opioid receptors, as well as in the suppression of the activity of tachykinin receptors and TRPV1 and TRPM8 ion channels, in the therapy of inflammatory, autoimmune diseases, gastrointestinal tract diseases, respiratory tracts and cough.

DISCLOSURE OF THE INVENTION

It is an object of the present invention to provide a novel drug that is an agonist of opioid receptors (μ, delta and kappa), antagonists of tachykinin receptors ($NK_1$, $NK_2$ and $NK_3$), and TRPV1 and TRPM8 ion channels, said drug is effective for the treatment of inflammatory and autoimmune diseases, gastrointestinal tract diseases, respiratory tracts diseases and cough.

The technical result of the present invention is the development and production of effective agonist of opioid receptors, antagonists of tachykinin receptors and of TRPV1 and TRPM8 ion channels, which makes it possible to use the compound in the oral and topical application for the treatment of cough, asthma, COPD, bronchitis, rhinitis, diarrhea, irritable bowel syndrome, Crohn's disease, colitis, psoriasis, atopic dermatitis, pruritus, as well as other diseases associated with the activity of opioid and tachykinin receptors and of TRPV1 and TRPM8 ion channels.

The above technical result is achieved by using a 2-phenylethylamide N-(p-hydroxyphenylacetyl)phenylalanine compound (Compound I)

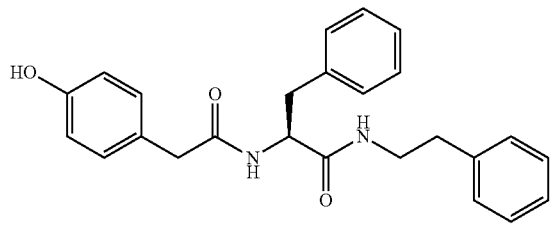 [SMILES: O=C(Cc1ccc(O)cc1)N[C@@H](Cc1ccccc1)C(=O)NCCc1ccccc1]

or an adduct, hydrate, solvate as an agonist of opioid receptors, antagonist of tachykinin receptors, as well as of TRPV1 and TRPM8 ion channels.

The present invention also relates to a modulator of opioid and tachykinin receptors, as well as of TRPV1 and TRPM8 ion channels, that represents Compound I.

The invention also relates to a process for the preparation of a 2-phenylethylamide N-(p-hydroxyphenylacetyl)phenylalanine compound.

The present invention also relates to the use of a 2-phenylethylamide N-(p-hydroxyphenylacetyl)phenylalanine compound or an adduct, hydrate, solvate thereof for the preparation of a pharmaceutical composition for the prevention and/or treatment of inflammatory, autoimmune diseases, gastrointestinal diseases, respiratory diseases, cough, such as asthma, COPD, bronchitis, rhinitis, diarrhea, irritable bowel syndrome, Crohn's disease, colitis, and also other diseases associated with the activity of opioid receptors, tachykinin receptors ($NK_1$, $NK_2$ and $NK_3$), TRPV1 and TRPM8 ion channels.

Furthermore, the invention relates to a pharmaceutical composition for the prevention and/or treatment of diseases, respiratory diseases, urinary tract diseases, gastrointestinal disease, cough, such as asthma, COPD, bronchitis, rhinitis, irritable bowel syndrome, Crohn's disease, colitis, psoriasis, atopic dermatitis, prurigo, as well as other diseases associated with the activity of opioid and tachykinin receptors, as well as TRPV1 and TRPM8 ion channels, the pharmaceutical composition comprising an effective amount of Compound I according to the invention and at least one pharmaceutically acceptable adjuvant. In some embodiments, the adjuvant is a pharmaceutically acceptable carrier and/or excipient.

The invention also comprises a method for preventing and/or treating a disorder associated with the activity of opioid, tachykinin receptors, and TRPV1 and TRPM8 ion channels in a subject in need of such treatment, the method comprising administering the pharmaceutical composition according to the invention to said subject. In some non-limiting embodiments of the invention, the disease is cough, asthma, COPD, bronchitis, rhinitis, diarrhea, irritable bowel syndrome, colitis, psoriasis, atopic dermatitis. In particular embodiments of the invention, the organism is an organism of a human or an animal.

The invention relates to a method of preventing and/or treating a disorder associated with the activity of opioid, tachykinin receptors and TRPV1 and TRPM8 ion channels in a subject in need of such treatment, the method comprising administering a therapeutically effective amount of Compound I to said subject.

The invention also relates to a method for preventing and/or treating cough, asthma, COPD, bronchitis, rhinitis, diarrhea, irritable bowel syndrome, Crohn's disease, colitis, psoriasis, atopic dermatitis, prurigo in a subject in need of such treatment, the method comprising administering a therapeutically effective amount of Compound I to said subject.

The invention also relates to the use of Compound I in the manufacture of a medicament.

The present also invention relates to a combination comprising Compound I in combination with one or more other additional therapeutic agents.

DETAILED DESCRIPTION OF THE INVENTION

Compound I of the present invention can be prepared using various well-known synthetic techniques, including using the synthetic techniques described below.

In the course of screening pharmacological targets of Compound I it has surprisingly been found that Compound I is an agonist of opioid μ-, delta- and kappa-receptors, an antagonist of a first, second and third type tachykinin receptor and a blocker of TRPV1 and TRPM8 ion channels. In accordance with the spectrum of experimentally determined therapeutic targets of Compound I, indications were determined in which the use of Compound I was the most promising. It has been found that the use of Compound I is prospectively for the therapy of inflammatory, autoimmune diseases (such as psoriasis, atopic dermatitis, Crohn's disease, ulcerative colitis), gastrointestinal disorders (such as diarrhea, irritable bowel syndrome), respiratory diseases (such as cough, asthma, COPD, bronchitis, rhinitis), and also prurigo.

Thus, Compound I is the novel agonist of opioid receptors, an antagonist of tachykinin receptors and of TRPV1 and TRPM8 ion channels, it can be used for the treatment of cough, asthma, COPD, bronchitis, rhinitis, diarrhoea, irritable bowel syndrome, Crohn's disease, colitis, psoriasis, atopic dermatitis, prurigo.

Terms and Definitions

The term «Compound I» relates to a 2-phenylethylamide N-(p-hydroxyphenylacetyl)phenylalanine that is also represented by the structural formula:

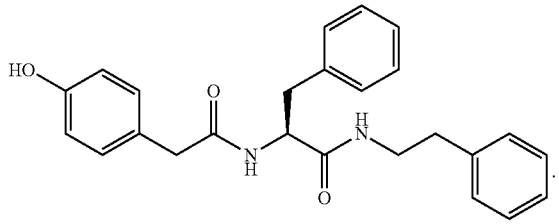 [SMILES: O=C(Cc1ccc(O)cc1)N[C@@H](Cc1ccccc1)C(=O)NCCc1ccccc1]

The term «C» when it is used with the reference to a temperature means centigrade scale or Celsius temperature scale.

The term «$IC_{50}$» means the concentration of the compound under the test, at which the half-maximal inhibition of an enzyme is achieved.

The term «pharmaceutically acceptable adducts» or «adducts» includes a product of a direct addition of molecule to each other, which are obtained using relatively nontoxic compounds. Examples of pharmaceutically acceptable nontoxic adducts may be adducts formed by untoxic nitro derivatives or urea. Other pharmaceutically acceptable adducts are adducts of nonionic tensides, cyclodextrines and others, and also charge-transfer complexes (t-adducts). It is necessary to note that the term "adducts" also includes nonstoichiometric adducts.

The term «solvate» is used for describing a molecular complex comprising the compound according to the invention and one or more molecules of a pharmaceutically acceptable solvent, for example, ethanol. The term «hydrate» is used when the indicated solvent is water.

The term «aberrant stimulation» of sensory nerve endings in the present document is the stimulation that significantly differs from a baseline in the body in the absence of pathology. The aberrant stimulation may be caused by overflow of immune system cells to the organ or tissue, the abnormality of processes resulting in the stimulation of sensory nerve endings, and also other factors.

The term «adjuvant» means any inorganic or organic pharmaceutically acceptable substance that is present in the formulation of a medicament or is used in the process of producing, manufacturing a medicament to impart to it necessary physicochemical properties.

The terms «treatment», «therapy» encompass the treatment of pathological conditions in mammals, preferably in human, and comprise: a) reducing, b) blocking (arresting) the course of disease, c) ameliorating the severity of disease, i.e. the induction of the regression of the disease, d) reversing the disease or condition to which the term is used, or one or more symptoms of the disease or condition.

The terms «prophylaxis», «prevention» encompasses the elimination of risk factors, and also the prophylactic treatment of sub-clinical stages of the disease in mammals, preferably in human, directed to the decrease in the probability of likelihood of occurrence of clinical stages of the disease. Patients for the prophylaxis therapy are selected on the basis of factors, which on the basis of known data involve the increase in the risk of origin of clinical stages of the disease as compared to the population. The preventive therapy is a) primary prevention and b) secondary prevention. The primary prevention is defined as the preventive treatment in patients who have not yet reached the clinical stage of the disease. The secondary prevention is the prevention of recurrence of the same or similar clinical condition of the disease.

Compound I that is an object of the invention is perspective for treating diseases associated with the aberrant stimulation of sensory nerve endings and the activity of mediators mediated by the action thereof on opioid receptors, tachykinin receptors ($NK_1$, $NK_2$ and $NK_3$), TRPV1 and TRPM8 ion channels, in particular, for the therapy of respiratory diseases (such as cough, asthma, chronic bronchitis, rhinitis), gastrointestinal diseases (such as irritable bowel syndrome, Crohn's disease, colitis, postoperative intestinal obstruction), systemic and local urinary diseases, including provided by initial pathological changes, or associated with various diseases or chronic administration of some drugs.

In some particular embodiments, compounds according to the invention may be used for treating other diseases associated with the aberrant situation of sensory nerve endings.

Method of Therapeutic Use of Compounds

It is an object of the invention also includes the administration to a subject in need of corresponding treatment of a therapeutically effective mount of the compound according to the invention.

The therapeutically effective amount means such an amount of a compound that is administered or delivered to a patient at which the desired response to the treatment (prophylaxis) in the patient most likely becomes apparent. The exact required amount may vary from subject to subject, depending on the age, body weight and general condition of the patient, the severity of disease, a method of the administration of a drug, the combination treatment using other drugs, and the like.

A compound of the invention or a pharmaceutical composition comprising a compound can be administered to a patient in any amount (preferably, the daily dose of the active substance is up to 0.5 g per a patient per day, most preferably the daily dose is 5-50 mg/day) and by any route of administration (preferably an oral route of the administration) effective to treat or prevent a disease.

After mixing the drug with a specific suitable pharmaceutically acceptable carrier at the desired dosage, compositions of the invention can be administered to a human or other animals orally, parenterally, topically (by inhalation, intranasally, epicutaneously), and the like.

The administration can be carried out both once and several times daily, weekly (or for any other time interval), or from time to time. Furthermore, one or more compounds may be administered to a patient daily for a specific period of days (e.g. 2-10 days), followed by a period without the intake of the drug (e.g., 1-30 days).

In case when the compound of the invention is used as part of the combination therapy regimen, a dose of each of components of the combination therapy is administered for the desired treatment period. The compounds that constitute the combination therapy can be administered to the patient's body both simultaneously, in the form of a dosage containing all the components, and in the form of individual dosages of the components.

Pharmaceutical Compositions

The invention also relates to pharmaceutical compositions which comprise the compound according to the invention (or a prodrug or other pharmaceutically acceptable derivative) and one or more pharmaceutically acceptable carriers, adjuvants, solvents and/or excipients, such which can be administered to the patient's body in combination with the compound that is the essence of the present invention and which do not have an influence on the pharmacological activity of the compound and are non-toxic when are administered in doses sufficient to deliver the therapeutical amount of the compound.

Pharmaceutical compositions claimed in the invention comprise the compound according to the invention in combination with pharmaceutically acceptable carriers, which may comprise any solvents, diluents, dispersions or suspensions, surfactants, isotonic agents, thickeners and emulsifiers, preservatives, cohesive materials, glidants and the like, suitable for the particular form of dosing. Materials which may serve pharmaceutically acceptable carriers comprise, but are not limited to mono- and oligosaccharides, and also derivatives thereof; gelatin; talc; excipients such as cacao oil and wax for suppositories; oils such as peanut, cottonseed, safflower, sesame, olive, corn and soybean oils; glycols such as propylene glycol; esters such as ethyl oleate and ethyl laurate; agar; buffering agents such as magnesium hydroxide and aluminum hydroxide; alginic acid; pyrogen-free water; isotonic solution, Ringer's solution; ethyl alcohol and phosphate buffers. The composition may also comprise other non-toxic compatible lubricants, such as sodium lauryl sulfate and magnesium stearate, as well as colorants, film formers, sweeteners, flavors and flavourings, preservatives and antioxidants.

The subject of this invention is also dosage forms, namely a class of pharmaceutical compositions, the formulation of which is optimized for a specific route of the administration to the body in a therapeutically effective dose, for example, for the administration to the body orally, topically, by inhalation, for example, in the form of an inhalation spray, or by an intravascular route, intranasally, subcutaneously, intramuscularly, as well as by infusion method, in the recommended dosages.

Pharmaceutical dosage forms of the present invention may comprise formulations obtained by methods of the use of liposome, by microencapsulation methods, a method of the preparation of nanoforms, or by other methods known in the pharmaceutical industry.

When preparing the composition, for example in the form of a tablet, an active principle is mixed with one or more pharmaceutical excipients such as gelatin, starch, lactose, magnesium stearate, talc, silica, gum arabic, mannitol, microcrystalline cellulose, hypromellose or similar compounds.

Tablets can be coated with sucrose, a cellulose derivative, or other materials suitable for coating. The tablets can be prepared in a variety of ways such as direct compression, dry or wet granulation, or hot fusion.

A pharmaceutical composition in the form of a gelatin capsule can be obtained by mixing the active principle with other substances and filling the resulting mixture into soft or hard capsules.

For the parenteral administration, aqueous suspensions, isotonic saline solutions, or sterile injectable solutions are used, they contain pharmacologically compatible agents, for example propylene glycol or butylene glycol.

Examples of Pharmaceutical Compositions

A substance described in the invention may be used for the prevention and/or treatment of diseases in human or animals in the form of the following formulations (the active ingredient is means as the «Substance»):

| Tablet I | mg/tablet |
|---|---|
| Substance | 0.5 |
| Microcrystalline cellulose | 66.5 |
| Sodium carboxymethylstarch | 2.3 |
| Magnesium stearate | 0.7 |

| Tablet II | mg/tablet |
|---|---|
| Substance | 0.5 |
| Microcrystalline cellulose | 62.0 |
| Sodium carboxymethylstarch | 2.3 |
| Magnesium stearate | 0.7 |

| Tablet III | mg/tablet |
|---|---|
| Substance | 50 |
| Microcrystalline cellulose | 620 |
| Sodium carboxymethylstarch | 23 |
| Magnesium stearate | 7 |

| Tablet IV | mg/tablet |
|---|---|
| Substance | 50 |
| Lactose Ph. Eur | 223.75 |
| Sodium croscarmellose | 6.0 |
| Corn starch | 15 |
| Polyvinylpyrrolidone (5% w/v paste) | 2.25 |
| Magnesium stearate | 3.0 |

| Tablet V | mg/tablet |
|---|---|
| Substance | 200 |
| Lactose Ph. Eur | 182.75 |
| Sodium croscarmellose | 12.0 |
| Corn starch (5% w/v paste) | 2.25 |
| Magnesium stearate | 3.0 |

| Capsule | mg/capsule |
|---|---|
| Substance | 10 |
| Lactose Ph. Eur | 488.5 |
| Magnesia | 1.5 |
| Substance | 10 |
| Lactose Ph. Eur | 488.5 |
| Magnesia | 1.5 |

| Intranasal formulation I | mg/mL |
|---|---|
| Substance | 1.0 |
| Sodium citrate dihydrate | 3.823 |
| Citric acid monohydrate | 0.609 |
| Glycerol | 25.0 |
| Dextrose | 5.5 |
| Benzyl alcohol | 2.5 |
| Water | up to 100% |

| Intranasal formulation II | mg/mL |
|---|---|
| Substance | 1.0 |
| Sodium citrate dihydrate | 3.823 |
| Citric acid monohydrate | 0.609 |
| Glycerol | 25.0 |
| Dextrose | 5.5 |
| Water | up to 100% |

| Intranasal formulation II | mg/mL |
|---|---|
| Substance | 1.0 |
| Sodium dihydrogen phosphate dihydrate | 3.38 |
| Disodium hydrogen phosphate dihydrate | 2.08 |
| Glycerol | 25.0 |
| Dextrose | 5.5 |
| Benzyl alcohol | 2.5 |
| Water | up to 100% |

| Intranasal formulation II | mg/mL |
|---|---|
| Substance | 1.0 |
| Sodium dihydrogen phosphate dihydrate | 3.38 |
| Disodium hydrogen phosphate dihydrate | 2.08 |
| Glycerol | 25.0 |
| Dextrose | 5.5 |
| Water | up to 100% |

| Inhalable formulation | mg/mL |
|---|---|
| Substance | 2.0% w/v |
| Glycerol | 20.0% w/v |
| Water for injections | up to 100% |

These formulations may be prepared in accordance with standard pharmaceutical procedures. Tablets (I)-(II) can be coated by an enteric coating with the use of, for example, cellulose acetate phthalate.

Use of Compound I in Combination Therapy

Regardless of the fact that Compound I according to the invention may be administered as an individual active pharmaceutical agent, it may also be used in combination with one or more other agents, in particular the other agent may represent a cough reflex suppressant (codein, glaucine, butamirate, bitiodin), a mucolytic agent (bromhexine, ambroxol), a mucoregulatory agent (carbocisteine), an expectorant (thyme, potassium iodide, broncholytin), an antibiotic, NSAID or other anti-inflammatory agent and the like. In case of ingestion together, therapeutic agents may represent different pharmaceutical dosage forms which are administered simultaneously or sequentially at different time, or therapeutic agents may be combined into one pharmaceutical dosage form.

The phrase "combination therapy" in respect to compounds of the invention in combination with other pharmaceutical agents means the simultaneous or sequential administration of all agents that will somehow provide the beneficial effect of the combination of drugs. The co-administration implies, in particular, co-delivery, for example, in one tablet, capsule, injection or other form, having a fixed ratio of active substances, as well as the simultaneous delivery in several, separate dosage forms for each compound, respectively.

Thus, the administration of the compound of the invention can be carried out in combination with additional therapies known to those skilled in the field of the prevention and treatment of corresponding diseases, including the use of antibacterial and anti-inflammatory drugs, drugs for suppressing symptoms or side effects of one of the drugs.

If the pharmaceutical dosage form is a fixed dose, the combination uses the compound of the invention within an acceptable dose range. Compound I of the invention can also be administered to a patient sequentially with other agents, when the combination of these drugs is not possible. The invention is not limited to the sequence of administration; the compound of the invention can be co-administered to the patient's body before or after the administration of another drug.

PREPARATION OF COMPOUNDS ACCORDING TO THE INVENTION

Preparation of a 2-phenylethylamine N-(p-hydroxyphenylacetyl)phenylalanine

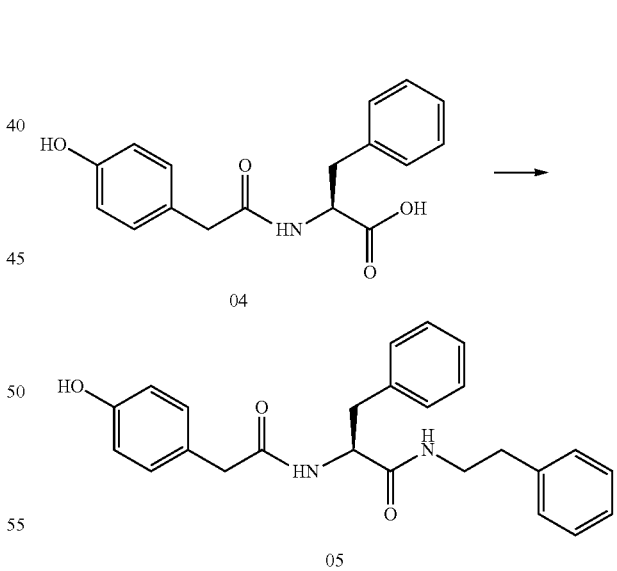

(S)-methyl 2-(2-(4-hydroxyphenyl)acetomido)-3-phenyl-propanoate (04) (1.50 g, 5.29 mmol), phenylethylamine (0.86 g, 6.35 mmol, 1.2 Eq), TBTU (2-(1H-benzotriazole-1-yl)-1,1,3,3-tetramethyluronium tetrafluoroborate) (2.04 g, 6.35 mmol, 1.2 Eq) and triethylamine (0.64 g, 6.35 mmol, 1.2 Eq) are dissolved in 20 ml of dry acetonitrile and admixed at room temperature for 5 hours. The reaction mass was diluted with 3% solution of potassium carbonate (500 ml) and extracted with dichloromethane (2×40 ml). The extract was washed out with water, was dried by sodium sulfate, the solvent was removed in vacuum. The residue obtained after the evaporation (1.65 g) was purified with the aid of preparative HPLC. As the result, 1.1 g of a product having the purity of 99% by data of analytic HPLC was prepared.

APCI-MS (m/z (intensity)): 402.90 ([M+H]$^+$, 100%).

$^1$H NMR (400 MHz, DMSO-d$_6$) δ 9.05 (s, 1H), 7.94-7.83 (m, 2H), 7.30-7.09 (m, 10H), 6.92-6.84 (m, 2H), 6.64-6.56 (m, 2H), 4.43 (td, J=8.8, 5.2 Hz, 1H), 3.36-3.12 (m, 4H), 2.90 (dd, J=13.7, 5.2 Hz, 1H), 2.79-2.60 (m, 3H).

The Characteristic of Biological Activity of Compounds According to the Invention The biological activity of Compound that is the object of the present invention was studied in different in vitro and in vivo experiments. In particular, upon the study of the activity of Compound I in different in vitro and in vivo models, the inhibitory effect of Compound I on the model of cough induced by the administration of capsaicin in guinea pigs has been.

Studies of the biological activity of Compound I in vitro have allowed to establish that Compound I is an agonist of opioid receptors, an antagonist of tachykinin receptors and of TRPV1 and TRPM8 ion channels. To all appearance, the activity of Compound I in models of cough, and also in different models of gastrointestinal disorders is associated with the influence on the aforesaid proteins.

Example 1. The Study of the Effect of Compound I on the Activity of Tachykinin Receptor Type 1

Compound I was dissolved in DMSO to a concentration of 100 mM; then the stock solution was serially diluted with DMSO. The maximal start concentration of substance is 100 μM. The effect was determined at 8 concentrations of test compound, each concentration was investigated twice. U373 cells expressing human NK$_1$R were used in the experiment, said cells after the preincubation with an agonist [Sar9,Met (O2)11]-SP (1 nM) were incubated with Compound I. The activity of receptors was determined by the intracellular calcium concentration using fluorescence spectroscopy (Glia. 1992; 6(2):89-95).

It has been established as the result of the study that Compound I is an antagonist of tachykinin receptor type 1 having IC$_{50}$=59 μM.

Example 2. The Study of the Effect of Compound I on the Activity of Tachykinin Receptor Type 2

Compound I was dissolved in DMSO to a concentration of 100 mM; then the stock solution was serially diluted with DMSO. The maximal start concentration of substance is 100 μm. The effect was determined at 8 concentrations of test compound, each concentration was investigated twice. CHO cells expressing human NK$_2$R were used in the experiment, said cells after the preincubation with an agonist [Nleu10]-NKA-(4-10) (10 nM) were incubated with the test compound. The activity of receptors was determined by the intracellular calcium concentration using fluorescence spectroscopy (Biochem Biophys Res Commun. 1994 May 16; 200(3):1512-20).

It has been established as the result of the study that Compound I is an antagonist of tachykinin receptor type 2 having IC$_{50}$=6.4 μM.

Example 3. The Study of the Effect of Compound I on the Activity of Tachykinin Receptor Type 3

Compound I was dissolved in DMSO to a concentration of 100 mM; then the stock solution was serially diluted with DMSO. The maximal start concentration of substance is 100 μM. The effect was determined at 5 concentrations of test compounds, each concentration was investigated twice. CHO-K1 cells expressing NK$_3$R were used in the experiment, said cells after the preincubation with an agonist [MePhe10]-NKB (1 nM) were incubated with the test compound. The activity of receptors was determined by the intracellular calcium concentration using fluorescence spectroscopy (Br J Pharmacol. 1999 October; 128(3):627-36).

It has been established as the result of the study that Compound I is an antagonist of tachykinin receptor type 3 having IC$_{50}$=15 μM.

Example 4. The Study of the Effect of Compound I on the Activity of μ-Opioid Receptor Compound I was dissolved in DMSO to a concentration of 100 mM; then the stock solution was serially diluted with DMSO. The maximal start concentration of substance is 300 μM. The effect was determined at 10 concentrations of test compounds, each concentration was investigated twice. A human recombinant μ-opioid receptor was used in the experiment, said receptor after the preincubation with an agonist [3H]DAMGO (0.5 nM) is then incubated with the test compound or 120 minutes. The activity of receptors was determined by the radioligand displacement method. It has been established as the result of the study that Compound I is an agonist of μ-opioid receptor having IC$_{50}$=4.1 μM.

Example 5. The Study of the Effect of Compound I on the Activity of Delta-Opioid Receptor Compound I was dissolved in DMSO to a concentration of 100 mM; then the stock solution was serially diluted with DMSO. The maximal start concentration of substance is 300 μM. The effect was determined at 10 concentrations of test compounds, each concentration was investigated twice. A recombinant human delta opioid receptor was used in the experiment, said receptor after the preincubation with an agonist [3H]DADLE (0.5 nM) is then incubated with the test compound for 120 minutes. The activity of receptors was determined by the radioligand displacement method. It has been established as the result of the study that Compound I is an agonist of delta-opioid receptor having IC$_{50}$=64 μM.

Example 6: The Study of the Effect of Compound I on the Activity of Kappa-Opioid Receptor Compound I was dissolved in DMSO to a concentration of 100 mM; then the stock solution was serially diluted with DMSO. The maximum start concentration of substance is 300 μM. The effect was determined at 10 concentrations of test compounds, each concentration was examined twice. The human recombinant delta opioid receptor was used in the experiment, said receptor after the preincubation with an agonist [3H]U69593 (0.5 nM) is then incubated with the test compound for 120 minutes. The activity of receptors was determined by the radioligand displacement method. It has been established as the result of the study that Compound I is an agonist of kappa opioid receptor having IC$_{50}$=7.1 μM.

Example 7. The Study of the Effect of Compound I on the Activity of TRPV1 Ion Channel Compound I was dissolved in DMSO to a concentration of 100 mM; then the stock solution was serially diluted with DMSO to prepare a test solution with the concentration of substance equal to 50 μM. TRPV1 expressing CHO cells were used in the experiment. At the day of the experiment, the cells were incubated with a 4 μM of a solution of fluorescent indicator Fluo-4 AM. The cells after the preincubation with Capsaicin (30 nM), the known agonist of TRPC1 ion channel, were incubated with the test compound. The activity of receptors was determined by the intracellular calcium concentration using fluorescence spectroscopy (Behrendt, H. J. et al. (2004), Br. J. Pharmacol., 141: 737-745. FINAL).

It has been established as the result of the study that Compound I is a blocker of TPRV1 ion channel having $IC_{50}=51$ μM.

Example 8. The Study of the Effect of Compound I on the Activity of TRPM8 Ion Channel Compound I was dissolved in DMSO to a concentration of 100 mM; then the stock solution was diluted with DMSO to prepare a test solution with the concentration of substance equal to 50 μM. TRPM8 expressing HEK293 cells were used in the experiment. At the day of the experiment, the cells were incubated with a 4 μM of a solution of fluorescent indicator Fluo-4 AM. The cells after the preincubation with Icilin (100 nM), the known agonist of TRPM8 ion channel, were incubated with the test compound. The activity of receptors was determined by the intracellular calcium concentration using fluorescence spectroscopy (Behrendt, H. J. et al. (2004), Br. J. Pharmacol., 141: 737-745. FINAL).

It has been established as the result of the study that Compound I is a blocker of TRPM8 ion channel having $IC_{50}=62$ μM.

Example 9. The Study of the Effect of Compound I on the Motility of the Gastrointestinal Tract In Vivo The effect of Compound I on the motility of the GIT was studied by a standard procedure (Li Y. Y., Li Y. N., Ni J. B., Chen C. J., Lv S., Chai S. Y., Wu R. H., Yüce B., Storr M. Involvement of cannabinoid-1 and cannabinoid-2 receptors in septic ileus//Neurogastroenterol Motil. 2010. V. 22. P. 350-388). The study was carried out on male balb/c mice, the individual weight of which deviates from the mean value within the sex of no more than ±20%. The animals were given the intragastric administration of a solution of activated carbon (50 mg/ml, in 10 ml/kg) and the rate (in minutes) of the movement of the activated carbon on the intestine of animals was evaluated. Compounds I was administered once intragastrically 1 hour prior to administration of activated carbon. As the comparative preparations, hyoscin butyl bromide (Buscopan) at a dose of 3 mg/kg, trimebutine (Trimedat) at a dose of 33 mg/kg, mebeverine (Duspatalin) at a dose of 30 mg/kg were used. The obtained data were checked using the Grubb's test for the presence of the largest or smallest abnormal observation (ejection) in the sample. Values determined "to be eliminated" in this test were not used for further assay. For all data, descriptive statistics was used: a mean value (M) and standard error of the mean value (m) were counted up. The normality of distribution of the values obtained in the course of the experiment was checked with the aid of the Kolmogorov-Smirnov test. In the case of normal distribution, Student's t-test (t-test) was used to evaluate the inter-group distinctions. In the case of the distribution that is other than the normal one for the comparison of several groups, the Kruskall-Wallis test (with Dann's post hoc test) was used. Distinctions were determined at 5% at a level of confidence. Results of the study are presented in Table 1

TABLE 1

The influence of Compound I on the motility of the gastrointestinal tract

| Groups | Regimen of the administration of preparations | n | The time of ejection of activated carbon, min |
|---|---|---|---|
| Intact | | 10 | 73.8 ± 3.7 |
| Compound I (15 mg/kg) | Once intragastrically 1 hour prior to the administration of activated carbon | 10 | 147.6 ± 8.94* |
| Compound I (7.5 mg/kg) | | 10 | 123.4 ± 11.43* |
| Compound I (3 mg/kg) | | 10 | 130.4 ± 11.42* |
| Compound I (1.5 mg/kg) | | 10 | 108.7 ± 9.28* |
| Hyoscine butyl bromide (3 mg/kg) | | 10 | 87.6 ± 4.75* |
| Trimebutine (33 mg/kg) | | 10 | 110.8 ± 6.52* |
| Mebeverine (30 mg/kg) | | 10 | 114.5 ± 12.22* |

Note:
*is the significance of the difference (P < 0.05) with the intact group

The administration of Compound I by 1.5-2 times increased the time of activated carbon evacuation in mice. The obtained data make it possible to conclude that Compounds I have the pronounced spasmolytic effect and is useful for the treatment of diarrhea, irritable bowel syndrome, as well as other diseases associated with the GIT dysmotility. The effect of Compound I outperforms the effect of hyoscin butyl bromide, trimebutine and mebeverine.

Example 10: The Study of the Activity of Compound I in the Stress-Induced Defecation Model in Rats The study of the activity of Compound I in the stress-induced defecation model was carried out by a standard procedure (Taguchi R., Shikata K., Furuya Y, Hirakawa T., Ino M., Shin K., Shibata H. Selective corticotropin-releasing factor 1 receptor antagonist E2508 reduces restraint stress-induced defecation and visceral pain in rat models//Psychoneuroendocrinology. 2017. P. 110-115).

Rats were adapted to a room in which the experiment was conducted for 24 hours. The study was carried out on satisfied rats. Compound I was administered once, intragastrically. After 1 hour, the rat was placed in the cloth so that the front paws were pressed to the body. In such a form, the rat was placed into the individual cage on the gating and was left for 40 minutes. Summarily the whole of excrement released during the observation period of 40 minutes then was weighed.

For all data, descriptive statistics is applied: the arithmetic mean (M) and the standard error of the mean (m) are counted up. The normality of distribution of the values obtained in the course of the experiment was checked with the aid of the Shapiro-Wilk test. In the case of normal distribution, 1-way ANOVA (with Dann's post hoc test) was used to evaluate the inter-group distinctions. In the case of the distribution that is other than normal one, the 1-way ANOVA (with Tukey's post hoc test) was used for the comparison of several groups.

Results of the study have showed that the intragastric administration of Compound I dose-dependently reduces the stress-induced defecation in rats. The obtained data makes it possible to conclude that Compound I has the pronounced spasmolytic effect and is useful for the therapy of irritable bowel syndrome accompanied by diarrhea.

TABLE 2

The influence of Compound I on the weight of excrement on the model of stress-induced defecation in rats (m ± t, p = 10)

| Groups | Dose, mg/kg | n | Weight of excrement, g |
|---|---|---|---|
| Intact | — | 10 | 0.24 ± 0.05 |
| Control | — | 10 | 2.65 ± 0.35* |
| Compound I | 0.3 | 10 | 2.35 ± 0.35* |
| | 1 | 10 | 1.43 ± 0.12 |
| | 3 | 10 | 1.00 ± 0.06& |

Note:
*significance of difference (P < 0.05) with the intact group
&significance of difference (P < 0.05) with control

Example 11. The Study of the Activity of Compound I on the Oxazolone-Induced Inflammatory Bowel Disease Model The study of the activity of Compound I on the oxazolone-induced inflammatory bowel disease model (ulcerative Colitis and Crohn's disease model) was carried out by means of a standard procedure (Heller F., Fuss I. J., Nieuwenhuis E. E., Blumberg R. S., Strober W. Oxazolone colitis, a Th2 colitis model resembling ulcerative colitis, is mediated by IL-13-producing NK-T cells//Immunity. 2002. P. 629-638).

The study was carried out on female balb/c mice. A 3.5 F catheter was introduced into the large intestine to a depth of 3-4 cm. Then, 150 µl of 1% oxazolone solution in 50% ethanol was slowly introduced into the colon lumen, the catheter was slowly removed and the mouse was kept in a vertical position (upside down) for 60 seconds to avoid the introduced solution flowing-out. Experimental animals were returned to the cages and the animal was kept in the warm. Compound I was administered intragastrically, three times: 1 hour, 25 hours and 49 hours after the rectal administration of oxazolone. 72 hours later after the rectal administration of oxazolone, the macroscopic assessment of intestinal wall damage is carried out with the help of score scale: 0 points—no lesions, 1 point—hyperemia, no ulcers, 2 points—hyperemia and thickening of the intestinal wall, no ulcers, 3 points—one ulcer without thickening of the intestine wall, 4 points—2 or more of the site of ulceration or inflammation, 5 points—2 or more severe sites of ulcerations and inflammation, or one site of ulceration/inflammation affecting >1 cm in length of the intestine, 6-10 points—the lesion affects >2 cm in length of the intestine, the score increases by 1 point per each 1 cm that is damaged.

For all data, descriptive statistics is applied: the arithmetic mean (M) and the standard error of the mean (m) are counted up. The normality of distribution of the values obtained in the course of the experiment was checked with the aid of the Shapiro-Wilk test. In the case of normal distribution, 1-way ANOVA (with Dann's post hoc test) was used to evaluate the inter-group distinctions. In the case of the distribution that is other than the normal one, the 1-way ANOVA (with Tukey's post hoc test) was used for the comparison of several groups. Distinctions were determined at 5% at a level of confidence. Results of the study are presented in Table 3.

Results of the study have showed that on the inflammatory bowel disease model Compound I at the intragastric administration has the pronounced therapeutic effect, in particular reduces the damage of the wall of the large intestine to the level of intact animals. The obtained data makes it possible to conclude that Compound I is useful for the therapy of Crohn's disease and ulcerative colitis.

TABLE 3

The influence of Compound I on colon wall damage on the oxazolone-induced ulcerative colitis model in mice (M ± m, n = 10)

| Groups | Dose, mg/kg | n | The degree of colon wall damage, points |
|---|---|---|---|
| Intact | — | 10 | 0.00 ± 0.00 |
| Control | — | 10 | 2.00 ± 0.21* |
| Compound I | 10 | 10 | 2.20 ± 0.96 |
| | 20 | 10 | 0.00 ± 0.00& |
| Prednisolone | 10 | 10 | 1.40 ± 0.37* |

Note:
*significance of difference (P <0.05) with the intact group
&significance of difference (P < 0.05) with control.

Example 12. The Study of the Activity of Compound I on the Acute Pain Response Model in Response to the Administration of Mustard Oil in Mice The study of the activity of the compound on the acute pain response model was conducted using a standard procedure (Laird M. A., Martinez-Caro L., Garcia-Nicas E., Cervero F. A new model of visceral pain and referred hyperalgesia in the mouse//J. Pain 92 (2001). P. 335-342).

The study was carried out on balb/c male mice, the individual weight of which deviates from the mean value within the sex of no more than ±10%. First, the mice were lightly anesthetized (after 24 hours of fasting). Then 1% solution of mustard oil in physiological solution was introduced to the animals at 4 cm in depth with the help of catheter 3.5 F. The solvent was introduced to the healthy control. 5 minutes after the introduction of the mustard oil, the presence of pain in the animal (a number of abdominal lickings, abdominal wall abductions, lower abdominal deformity to the floor, abdominal distension) was evaluated during the first 20 minutes. Compound I was administered once intragastrically 1 hour before the administration of mustard oil. The obtained data were checked using the Grubb's test for the presence of the largest or smallest abnormal observation (ejection) in the sample. Values determined "to be eliminated" in this test were not used for further assay. For all data, descriptive statistics was used: a mean value (M) and standard error of the mean value (m) were counted up. The normality of distribution of the values obtained in the course of the experiment was checked with the aid of the Kolmogorov-Smirnov test. In the case of normal distribution, Student's t-test (t-test) was used to evaluate the inter-group distinctions. In the case of the distribution that is other than the normal one the Kruskall-Wallis test (with Dann's post hoc test) was used for the comparison of several groups. Distinctions were determined at 5% at a level of confidence. Results of the study are presented in Table 4.

TABLE 4

The influence of Compound I on the number of pain sensations in the acute pain response model in response to the administration of mustard oil in mice.

| groups | Induction of pathology | Administration of the preparation | n | 0-20 min |
|---|---|---|---|---|
| Intact | Saline | | 10 | 2.2 ± 0.33 |
| Control | 1% mustard oil in saline | Once intragastrically 1 hour prior to the administration of mustard oil | 10 | 10.4 ± 1.59* |
| Compound I (15 mg/kg) | | | 10 | 2.56 ± 0.78 & |
| Compound I (7.5 g/kg) | | | 10 | 15.1 ± 1.7* |
| Compound I (3 g/kg) | | | 10 | 8.56 ± 0.94* |
| Compound I (1.5 g/kg) | | | 10 | 14.8 ± 3.01* |

Note:
*significance of difference (P < 0.05) with the intact group
& significance of difference (P < 0.05) with control The administration of Compound I has reduced to the level of intact values the number of pain sensations caused by the rectal administration of mustard oil to animals. The obtained data make it possible to conclude that Compound I has the pronounced analgesic effect in the pain syndrome in the intestine and thus Compound I is useful for the therapy of pain symptoms in irritable bowel syndrome, ulcerative colitis, Crohn's disease and other gastrointestinal diseases.

Example 13. The Study of the Activity of Compound I at the Inhalation Administration in a Capsaicin Cough Model in Guinea Pigs The capsaicin cough model of was realized according to a standard procedure (Tanaka M., Maruyama K. Mechanisms of Capsaicin- and Citric-Acid-Induced Cough Reflexes in Guinea Pigs//J Pharmacol Sci. 2005. V. 99. P. 77-82). The study was carried out on guinea pigs of Agouti line, the individual value of the weight of which deviates from the mean value within the sex by no more than ±10%. The guinea pig was placed in the plastic chamber. To induce cough, the animals were inhaled using nebulizer by a capsaicin solution at a concentration of 30 µM for 5 minutes. The solution for inhalation was prepared as follows: 1.2 mg of capsaicin was diluted in 20 ml of the mixture: 10% ethanol and 10% Tween-80. Compound I was administered once, by inhalation for 1 minute, 15 minutes before the inhalation with the capsaicin solution. The number of cough attacks was counted for 15 minutes after the capsaicin inhalation. The obtained data were checked using the Grubb's test for the presence of the largest or smallest abnormal observation (ejection) in the sample. Values determined "to be eliminated" in this test were not used for further assay. For all data, descriptive statistics was used: a mean value (M) and standard error of the mean value (m) were counted up. The normality of distribution of the values obtained in the course of the experiment was checked with the aid of the Kolmogorov-Smirnov test. In the case of normal distribution, Student's t-test (t-test) was used to evaluate the inter-group distinctions. In the case of the distribution that is other than the normal one the Kruskall-Wallis test with Dann's post hoc test was used for the comparison of several groups. Distinctions were determined at 5% at a level of confidence. Results of the study are presented in Table 5.

TABLE 5

The influence of Compound I on the number of cough attacks for 15 minutes on the capsaicin cough model in guinea pigs at the inhalation administration 15 minutes before the inhalation of capsaicin solution

| Groups | n | A number of cough attacks for 15 minutes from the start of inhalation (test) | Suppression of cough (% from the control) |
|---|---|---|---|
| Intact | 16 | 0.0 ± 0.0 | — |
| Control (placebo) | 18 | 15.2 ± 0.8* | — |
| Compound I (0.25 mg/kg) | 18 | 8.1 ± 0.2*& | 46.7 |

Note:
*significance of difference (P < 0.05) with the intact group
&significance of difference (P < 0.05) with control The inhalation administration of Compound I has significantly reduced the number of cough attacks for 15 minutes after the capsaicin inhalation to guinea pigs. The obtained results make it possible to conclude that Compound I has the pronounced antitussive effect.

Example 14. The Study of the Activity of Compound I at the Inhalation Administration on the Citrate Cough Model in Guinea Pigs The citrate cough model was realized according to the standard procedure (Tanaka M., Maruyama K. Mechanisms of Capsaicin- and Citric-Acid-Induced Cough Reflexes in Guinea Pigs//J Pharmacol Sci. 2005. V. 99. P. 77-82). The study was carried out on guinea pigs of Agouti line, the individual value of the weight of which deviates from the mean value within the sex by no more than ±10%. The guinea pig was placed in a plastic chamber. To induce cough, the animals were inhaled using nebulizer by a citric acid solution at a concentration of 0.4 m in saline for 10 minutes. Compound I was administered once, inhalation for 1 minute 15 minutes prior to the inhalation of citric acid solution. The number of cough attacks was calculated for 10 minutes of citric acid inhalation. The obtained data were checked using the Grubb's test for the presence of the largest or smallest abnormal observation (ejection) in the sample. Values determined "to be eliminated" in this test were not used for further assay. For all data, descriptive statistics was used: a mean value (M) and standard error of the mean value (m) were counted up. The normality of distribution of the values obtained in the course of the experiment was checked with the aid of the Kolmogorov-Smirnov test. In the case of normal distribution, Student's t-test (t-test) was used to evaluate the inter-group distinctions. In the case of the distribution that is other than the normal one the Kruskall-Wallis test (with Dann's post hoc test) was used for the comparison of several groups. Distinctions were determined at 5% at a level of confidence.

The inhalation administration of Compound I has significantly reduced the number of cough attacks for 10 minutes after the inhalation of the citric acid solution to guinea pigs. The pharmacological effect was manifested already 15 minutes after the administration of the test compound to the animals.

TABLE 6

The influence of Compound I on the number of cough attacks for 10 minutes on the citrate cough model in guinea pigs at the inhalation administration 15 minutes prior to the inhalation of citric acid solution

| Groups | n | A number of cough attacks during the inhalation for 10 minutes | Suppression of cough (% from the control of pathology) in the chamber |
|---|---|---|---|
| Intact | 10 | 0.3 ± 0.2 | — |
| Control (placebo) | 10 | 48.8 ± 4* | — |
| Compound I (0.25 mg/kg) | 10 | 29.7 ± 2.7*& | 39.1 |

Note:
*significance of difference (P < 0.05) with the intact group
&significance of difference (P < 0.05) with control The obtained results make it possible to conclude that Compound I has the pronounced antitussive effect at the inhalation administration characterized by a high rate of onset of the effect. Thus, Compound I may be used for the therapy of cough, and also other respiratory diseases such as COPD, bronchitis and asthma.

Example 15. The Study of Pharmacokinetics and Tissue Bioavailability of Compound I after the Oral Administration to Rats Since Compound I is an agonist of opioid receptors, its high systemic bioavailability and through the brain-blood barrier may potentially results in the development of side effects.

To confirm low systemic availability of Compound 1, the study of pharmacokinetics and bioavailability of Compound 1 was carried out after the oral administration to rats in a dose of 10 mg/kg. The study was carried out on 18 male Vistar rats. Blood sampling in the animals was carried out at given time points for 24 h after the administration of the preparation. The content of Compound 1 in plasma samples was analyzed by HPLC-MS/MS, the yield point was 1 ng/ml. The results of the study are shown in table 7.

TABLE 7

The study of pharmacokinetics and tissue bioavailability of Compound I after the oral administration to rates in a dose of 10 mg/kg

| Tissue | n | Maximal concentration of Compound I, ng/ml | Mean concentration for 24 hours, ng/ml |
|---|---|---|---|
| Blood plasma | 6 | 32.6 ± 30.5 | 5.5 |
| Brain | 6 | 0 ± 0 | 0.0 |

Since it has been shown in the source of in vitro studies that Compound I shows the modulating effect on opioid and tachykinin receptors being in a concentration above 1 μM, it is possible to assert that Compound I will not have any toxic effects upon the systemic administration. Furthermore, when administered in a therapeutic dose, Compound I does not penetrate into the brain of rats and may not have any effects on the CNS of the animals.

Example 16: The Study of Pharmacokinetics and Tissue Bioavailability of Compound I after the Oral Administration to Mice In order to confirm the low systemic availability of Compound 1 and to assess the tissue bioavailability of Compound 1 at the oral administration, the pharmacokinetics and bioavailability of Compound 1 after the oral administration at a dose of 10 mg/kg to mice were studied. Blood sampling in animals was carried out at given time points for 24 hours after the administration of the preparation. The content of Compound 1 in plasma samples was analyzed by HPLC-MS/MS, the yield point was 1 ng/ml. The results of the study are presented in table 8.

TABLE 8

The study of pharmacokinetics and tissue bioavailability of Compound I after the oral administration to mice in a dose of 10 mg/kg

| Tissue | n | Maximal concentration of Compound I, ng/ml | Mean concentration of Compound I for 24 hours, ng/ml |
|---|---|---|---|
| Blood plasma | 6 | 14.2 | 0.8 |
| Brain | 6 | 8.62 | 1.5 |
| Spinal cord | 6 | 96 | 11 |
| Lymphatic nodes | 6 | 81 | 9 |
| Heart | 6 | 32 | 3 |
| Muscles | 6 | 86 | 9 |
| Stomach | 6 | 34053 | 1853 |
| Small intestine | 6 | 5949 | 1331 |
| Large intestine | 6 | 5299 | 989 |

Since it has been shown in the course of in vitro studies that Compound I shows the modulating effect on opioid and tachykinin receptors at a concentration above 1 μM (i.e. more than 300 ng/ml), it is possible to assert that, when orally administered, Compound I will cause the pharmacological effect only on receptors located in the gastrointestinal tract tissues. Furthermore, the average concentration of the substance in the brain is about three orders of magnitude lower than the minimum effective concentration.

Example 17. The Study of the Effect of Compound I on the Functional State of the Central Nervous System of Mice For the final confirmation of the safety of Compound I at the oral administration, the study of the effect of Compound I on the functional state of the central nervous system of mice in the open field test was carried out. "Open field" test consists in the evaluation of motor and research activities, orientation reaction and emotional reactivity in the registration of spontaneous behaviour of animals. The study was carried out according to the standard technique (Buresh Y, Bureshova O., Joseph P. Houston. Methods and main experiments to study the brain and behavior (Moscow, 1991, pp. 119-122).

The study was carried out on male balb/c mice, the individual weight of which deviates from the mean value within the sex of no more than ±10%.

Compound I was administered once, intragastrically. The evaluation of the effect on the central nervous system was carried out 2 hours after the administration of Compound I in the study of the approximate research behaviour of mice in the "open field". The experimental "open field" facility was a chamber of 100×100×60 cm in size, with a square floor and white walls. The floor of the chamber is divided into 16 squares, in each square there is the round orifice having 6 cm in diameter. The chamber is illuminated by the incandescent electric lamp having a power of 100 watts, located at a height of 1 m from the floor of the chamber. The animal was placed in one of the corners of the chamber and for 15 minutes the number of horizontal squares crossed by it (horizontal activity), getting up on its hind legs (vertical activity), washing (grooming), and defecation by the number of fecal balls were recorded. Then the total motor activity was calculated, the activity was calculated as the sum of the crossed horizontal squares, standing on the hind legs and washing.

The obtained data were checked using the Grubb's test for the presence of the largest or smallest abnormal observation (ejection) in the sample. Values determined "to be eliminated" in this test were not used for further assay. For all data, descriptive statistics was used: a mean value (M) and standard error of the mean value (m) were counted up. The normality of distribution of the values obtained in the course of the experiment was checked with the aid of the Kolmogorov-Smirnov test. In the case of normal distribution, Student's t-test (t-test) was used to evaluate the inter-group distinctions. In the case of the distribution that is other than the normal one the Kruskalll-Wallis test with Dann's post hoc test was used for the comparison of several groups. Distinctions were determined at 5% at a level of confidence. Results of the study are presented in Table 9.

Compound I at the intragastric administration did not have the toxic influence on the values of approximate-research behaviour in mice in the "open field" test, as evidenced by the absence of statistically significant differences between indices of experimental and control groups of animals.

and intraperitoneally—2000 mg/kg did not cause death of animals. It has been shown that at the intragastric administration of Compound I in a dose of 5000 mg/kg and at the intraperitoneal administration—in a dose of 2000 mg/kg there is a lag in body weight gain, both in male and female mice and rats. Differences in the spontaneous behaviour, responses to the caused reactions of the experimental animals were not observed. Based on the obtained data, Compound I is the moderately toxic compound and belongs to the III class of toxicity according To GOST 12.1.007-76.

Thus, it has been shown in the course of the conducted studies that Compound 1 is the modulator of opioid and tachykinin receptors and of TRPV1 and TRPM8 ion channels. The influence on these therapeutic targets allows Compound 1 to have the pronounced therapeutic effect in the models of cough, abdominal pain, inflammatory and functional bowel diseases. The low systemic bioavailability and lack of penetration into the brain makes it possible to eliminate the occurrence of side effects that would occur in the systemic application of such a multi-drug.

Regardless of the fact that the invention is described with reference to the disclosed embodiments, it will be apparent to those skilled in the art that the specific experiments described in detail are merely presented for the purpose of illustrating the present invention and should not be construed as limiting the scope of the invention in any way. It

TABLE 9

The influence of Compound I on functional condition of the central nervous system of mice in the "open field" test at the intragastric administration 2 hours prior to the conduction of the study

| Group | n | Number of squares crossed within 15 minutes (horizontal activity) | Number of standing up on hind legs in 15 minutes (vertical activity) | The number of washes within 15 minutes (grooming) | General physical activity for 15 minutes | The number of acts of defecation within 15 minutes |
|---|---|---|---|---|---|---|
| Intact | 10 | 446.4 ± 19.4 | 72.5 ± 2.9 | 7.0 ± 2.2 | 525.9 ± 20.0 | 0.5 ± 0.3 |
| Control | 10 | 443.3 ± 15.6 | 67.1 ± 3.5 | 8.0 ± 1.5 | 518.4 ± 15.3 | 0.2 ± 0.1 |
| Compound I (0.75 mg/kg) | 10 | 468.5 ± 13.0 | 69.9 ± 4.3 | 7.2 ± 1.4 | 545.6 ± 16.5 | 0.2 ± 0.1 |
| Compound I (1.5 mg/kg) | 10 | 414.2 ± 24.1 | 63.0 ± 4.2 | 8.5 ± 1.6 | 485.7 ± 24.8 | 1.6 ± 0.6 |
| Compound I (2.5 mg/kg) | 10 | 459.5 ± 19.0 | 72.8 ± 3.5 | 8.6 ± 1.6 | 540.9 ± 18.0 | 0.0 ± 0.0 |
| Compound 1 (5 mg/kg) | 10 | 480.6 ± 22.1 | 71.7 ± 4.4 | 2.3 ± 1.0 | 554.6 ± 23.9 | 1.5 ± 0.2 |
| Compound 1 (10 mg/kg) | 10 | 449.2 ± 15.6 | 66.1 ± 3.3 | 6.8 ± 1.3 | 522.1 ± 16.5 | 0.0 ± 0.0 |
| Compound 1 (20 mg/kg r) | 10 | 479.4 ± 29.3 | 64.9 ± 4.0 | 6.2 ± 1.3 | 545.5 ± 30.4 | 0.0 ± 0.0 |
| Compound I (30 mg/kg) | 10 | 448.4 ± 16.4 | 69.0 ± 3.8 | 5.9 ± 1.4 | 523.3 ± 16.6 | 0.0 ± 0.0 |

Example 18. The Study of Acute Toxicity of Compound I at the Single Intragastric Administration The acute toxicity study was performed on 24 male and 24 female rats, and also on 24 male and 24 female mice. Before the administration of the Compound I, the body weight of the animals was recorded, after 1 hour of the administration, the state of the experimental animals was observed. Then, the body weights of rats and mice were recorded daily for 14 days after the administration of the substance, and the examination was carried out to detect the cases of death and abnormality in the state of the animals.

Compound I was administered to rats and mice intragastrically at a dose of 5000 mg/kg, intraperitoneally—at a dose of 2000 mg/kg. Control groups (female and male objects) were received a solvent (0.1% Tween-80 solution in water). A dose of 2000 mg/kg was intraperitoneally administered 2 times every 15 minutes in relation to the poor solubility of the compound.

Maximum possible doses of Compound I administered to male and female rats and mice intragastrically—5000 mg/kg should be understood that various modifications may be implemented without departing from the essence of the present invention.

The invention claimed is:

1. A compound of the formula

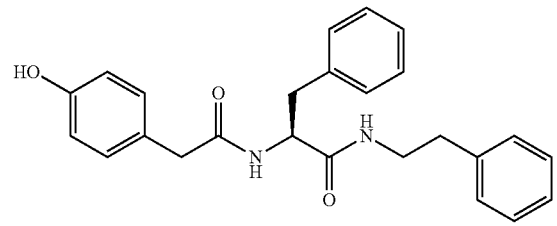 [SMILES: O=C(Cc1ccc(O)cc1)N[C@@H](Cc1ccccc1)C(=O)NCCc1ccccc1]

or a hydrate or solvate thereof.

2. An agonist of opioid receptors comprising the compound of claim 1.

3. A pharmaceutical composition for the treatment of a disorder associated with the activity of opioid and tachykinin receptors and TRPV1 and TRPM8 ion channels, comprising a therapeutically effective amount of the compound defined in claim 1 and at least one pharmaceutically acceptable carrier.

4. A pharmaceutical composition of claim 3, wherein the disorder associated with the activity of opioid and tachykinin receptors and TRPV1 and TRPM8 ion channels is cough, asthma, COPD, bronchitis, rhinitis, diarrhoea, irritable bowel syndrome, Crohn's disease, colitis, psoriasis, prurigo, atopic dermatitis and/or pruritus.

5. A combination comprising a therapeutically effective amount of the compound defined in claim 1 and one or more other additional therapeutic agents.

6. A combination of claim 5, wherein the other additional therapeutic agent is selected from an agent that inhibits the cough reflex, a mucolytic agent, a mucoregulatory agent, an expectorant, an antibiotic, an NSAID or an anesthetic.

7. An antagonist of tachykinin receptors comprising the compound of claim 1.

8. An antagonist of TRPV1 and TRPM8 ion channels comprising the compound of claim 1.

\* \* \* \* \*